United States Patent [19]

Macemon et al.

[11] 4,090,789
[45] May 23, 1978

[54] CUVETTE POSITIONING DEVICE FOR OPTICAL ANALYTICAL APPARATUS

[75] Inventors: James H. Macemon, Glen Burnie; Charles Soodak, Silver Spring, both of Md.

[73] Assignee: Baxter Travenol Laboratories, Inc., Deerfield, Ill.

[21] Appl. No.: 702,473

[22] Filed: Jul. 6, 1976

[51] Int. Cl.² ............................................... G01J 3/30
[52] U.S. Cl. ........................................ 356/85; 250/458; 356/96; 356/246
[58] Field of Search ................... 356/51, 78, 96–98, 356/201, 204, 205, 212, 179, 180, 244, 246, 85; 250/574, 576, 458, 461 A, 461 B

[56] References Cited

U.S. PATENT DOCUMENTS

| | | |
|---|---|---|
| 2,312,010 | 2/1943 | Van den Akker ..................... 356/78 |
| 2,984,146 | 5/1961 | Kwart et al. .......................... 356/51 |
| 3,241,432 | 3/1966 | Skeggs et al. ..................... 250/576 X |
| 3,589,814 | 6/1971 | Patterson et al. ..................... 356/96 |
| 3,680,957 | 8/1972 | Fukuda .................................. 356/97 |
| 3,854,050 | 12/1974 | Peterson et al. ................. 250/461 B |

FOREIGN PATENT DOCUMENTS 246,050  4/1912  Germany .............................. 356/180

*Primary Examiner*—F. L. Evans
*Attorney, Agent, or Firm*—Henry W. Collins; Eugene M. Cummings; Richard G. Kinney

[57] ABSTRACT

Cuvette positioning apparatus for use in a spectrophotometer adapted for comparing first and second material samples includes a carrier in which cuvettes to be alternately analyzed are arranged end-to-end. The carrier is reciprocated along a vertical axis to expose the cuvettes in alternation to the monochromatic beam of the apparatus. The rate of reciprocation is selected to avoid cavitation of the samples, and a sinusoidal drive arrangement increases the exposure time of the samples to the light beam and minimizes transit time for optimum measurement efficiency. Circuitry responsive to synchronizing signals derived from the drive arrangement is utilized to form an output signal indicative of the difference in measured characteristics between the samples.

13 Claims, 10 Drawing Figures

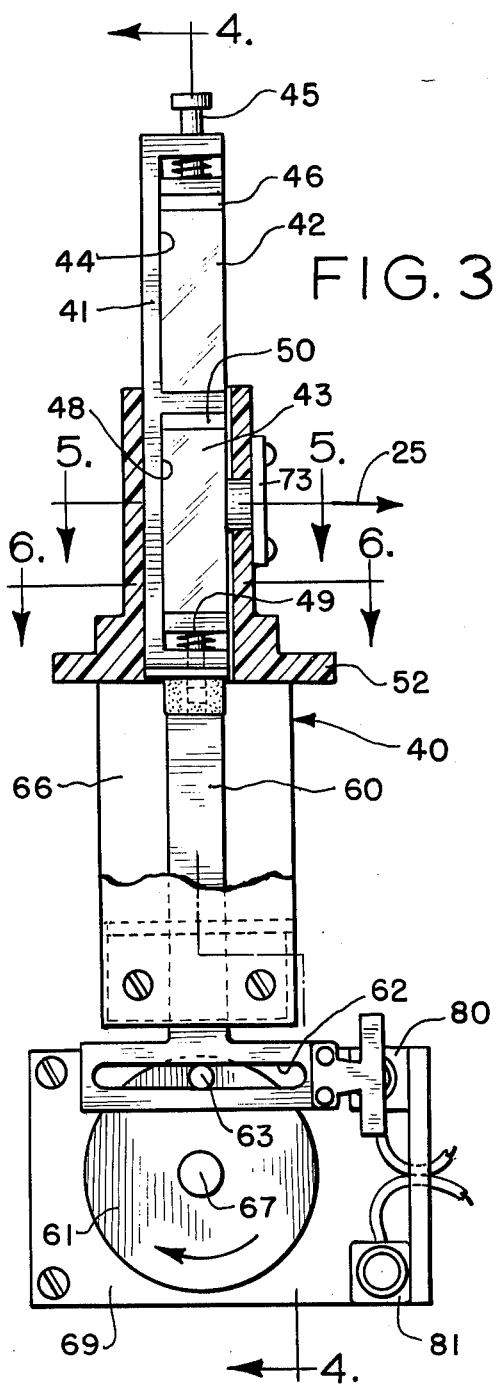
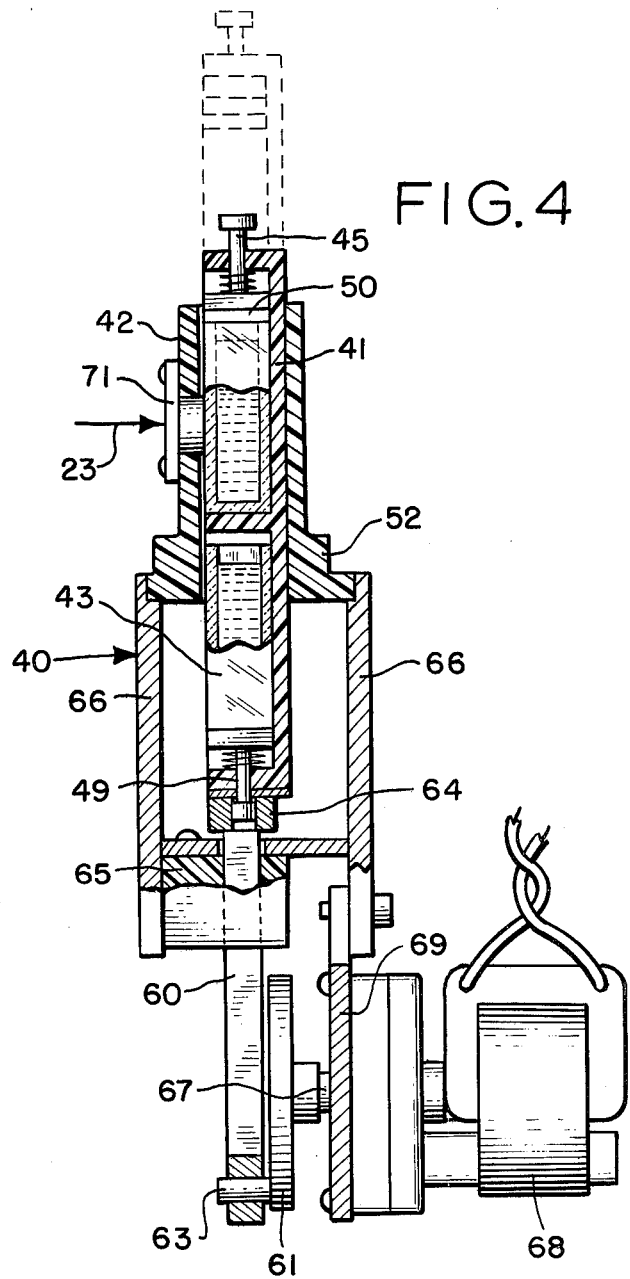
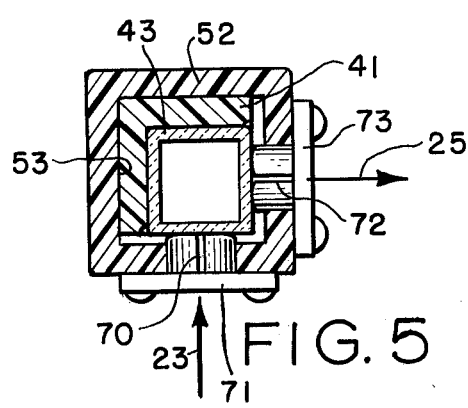
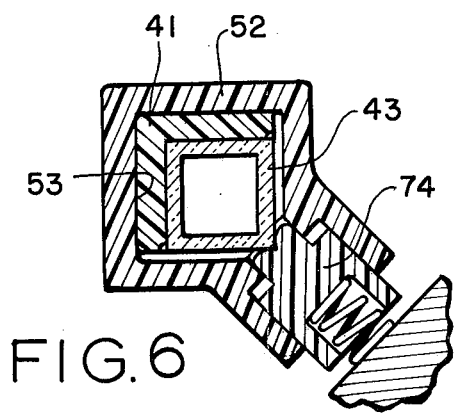

4,090,789

CUVETTE POSITIONING DEVICE FOR OPTICAL ANALYTICAL APPARATUS

BACKGROUND OF THE INVENTION

The present invention is directed generally to spectrophotometric apparatus, and more particularly, to a system and apparatus for spectrophotometrically comparing material samples with improved efficiency.

It is advantageous in many biological, physiological and chemical analysis applications to be able to make rapid spectrophotometric comparisons of fluid samples. One such application is in tracing the source of water pollutants, since many of the commonly encountered pollutant materials such as oil exhibit unique repeatable fluorescent characteristics, readily measured by conventional spectrofluorometric techniques. The suspected material, when excited by a light of constant wavelength, responds by emitting light in another, longer wavelength. By exposing the sample to a light source of variable wavelength and plotting the intensity of the emitted light at a selected wavelength, a unique characteristic plot, or signature, can be obtained for the material.

To positively identify two samples as having the same origin, a comparison can be made between their signatures. While this can be accomplished by plotting the emission characteristics of each sample separately and then carefully comparing the resulting plots, this procedure is time-consuming and subject to error, particularly where a large number of samples must be compared and the comparison must be accomplished by non-trained personnel or under adverse conditions. Accordingly, the need has arisen for spectrofluorometric and spectrophotometric apparatus which efficiently compares two samples and provides an output indicative of the difference between the samples.

In the past, comparison of samples in spectrophotometric apparatus has been accomplished by either positioning the samples to be compared at separate positions in the apparatus and alternately redirecting the excitation light beam to each sample, or by alternately positioning the samples in the light beam. In the former method, the light beam was redirected by means of mechanical choppers or mirrors to alternately impinge on the selected one of the samples, the light emitted from the samples being directed to a common photomultiplier tube from which the output signals are electrically processed to develop the differential output signal.

Neither of these procedures has proven entirely satisfactory. In the case where the light beam is chopped, it is difficult to maintain optical uniformity between the two light paths, since variations in the positioning or characteristics of any element not common to the two paths will effect the output signal developed by the apparatus. In the case where the cuvettes are physically repositioned, the difficulty of alternately indexing the fluid samples into position without subjecting them to forces which would affect their light-emitting or light-transfer characteristics necessitated slow transfer times and short residence periods in the beam, thereby reducing the efficiency of the apparatus and the accuracy of the comparison measurement.

The present invention is directed to a system and apparatus wherein a comparison between two samples is achieved by rapid vertical positioning of samples in a single light path, thus avoiding variations while maintaining high efficiency in the measurement procedure.

SUMMARY OF THE INVENTION

The invention is directed to a system for optically analyzing first and second material samples contained in individual cells. The system includes means for generating an analytical radiation beam for application to the samples, a cell carriage for supporting the cells in vertically aligned relationship, mounting means for the cell carriage defining a vertical path of reciprocation whereby the cells are individually exposed to the beam as the cell carriage traverses the path, and drive means for reciprocating the cell carriage along the path to alternately expose the cells to the beam.

BRIEF DESCRIPTION OF THE DRAWINGS

The features of the present invention, which are believed to be novel, are set forth with particularity in the appended claims. The invention, together with the further objects and advantages thereof, may best be understood by reference to the following description taken in connection with the accompanying drawings, in the several figures of which like reference numerals identify like elements, and in which:

FIG. 3 is a front elevational view, partially in cross-section, of the sample positioning apparatus of the invention.

FIG. 4 is a cross-sectional view of the sample positioning apparatus taken along line 4—4 of FIG. 3.

FIG. 5 is a cross-sectional view of the sample positioning apparatus taken along line 5—5 of FIG. 3.

FIG. 6 is a cross-sectional view of the sample positioning apparatus taken along line 6—6 of FIG. 3.

DESCRIPTION OF THE PREFERRED EMBODIMENT

Figure 1:
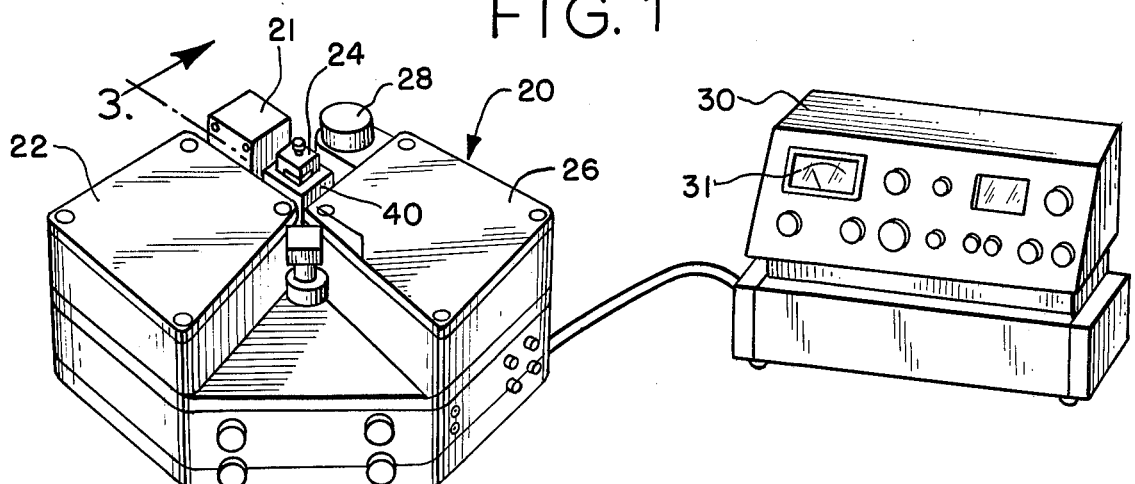
FIG. 1 is a perspective view of a spectrofluorometer incorporating a sample comparison system and apparatus constructed in accordance with the invention.
Figure 2:
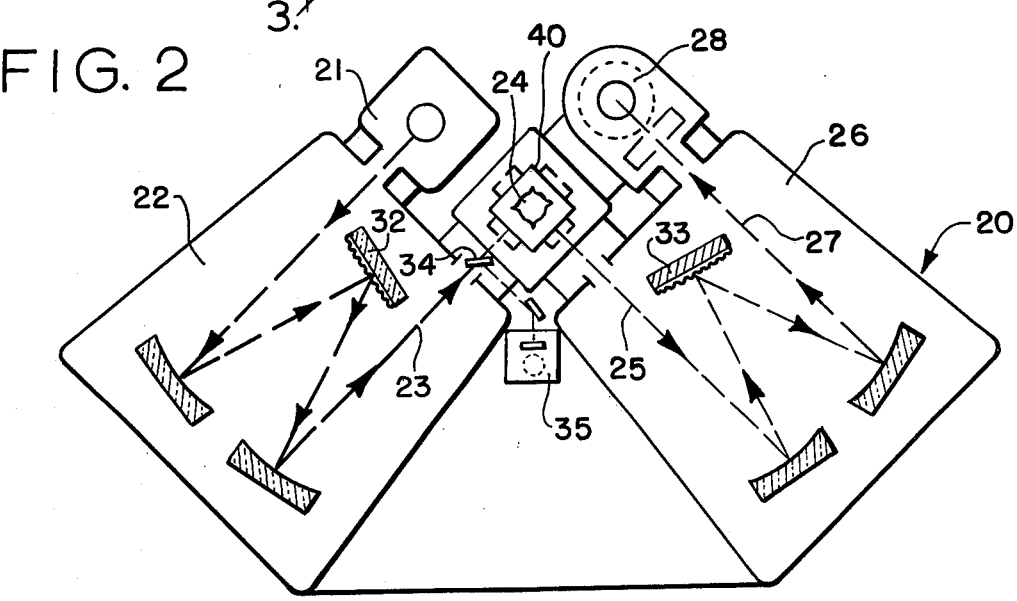
FIG. 2 is a diagrammatic view of the spectrofluorometer useful in understanding the operation of the invention.

Referring to the figures, and particularly to FIGS. 1 and 2, the invention is shown in conjunction with a spectrofluorometric sample comparison system incorporating a spectrofluorometer 20 which, except for its sample positioning apparatus, may be conventional in design and construction.

Spectrofluorometer 20 includes a suitable radiation source 21, such as a xenon light source, which furnishes light to an excitation monochromator 22 of the wavelength scanning type from which an excitation beam 23 of selected wavelength is directed to a cell 24 containing a quantity of fluid for analysis. The fluorescent emission beam 25 from the sample extends to an emission monochromator 26, also of the wavelength scanning type. The emission output beam 27, which comprises a characteristic wavelength contained in the emission beam 25 selected by scanning monochromator 26, is delivered to radiation detection means in the form of a photomultiplier tube 28 which generates a current signal corresponding to the intensity of the emission wavelength component from monochromator 26.

The signal from photomultiplier tube 28 is fed to a photometer apparatus 30 wherein it is converted to a voltage signal, amplified, and demodulated to form an output signal indicative of the difference between the samples. This output signal is applied to a suitable indicator such as a meter 31, an oscilloscope (not shown), an X-Y chart recorder (not shown) or a digital printer (not shown).

To provide for user-adjustment of the excitation and emission wavelengths, the gratings 32 and 33 of monochromators 22 and 25 are rotatable from the exterior of the apparatus. In spectrofluorometer 20 multiple rotation speeds are provided by motor driven cams (not shown) which shift the position of spring-loaded arms to shift the gratings so that a desired wavelength of excitation or emission is obtained. Concave mirrors are provided within the monochromators to direct the light beam to and from the gratings.

To facilitate use of the spectrofluorometer with an external plotting or display apparatus, each of the gratings may have associated with it a potentiometer for generating a direct current signal indicative of the position of the grating, and hence the wavelength selected by the monochromator. When the signal produced by the emission monochromator is connected to the X input of a plotter, and the excitation monochromator is set at a wavelength for maximum excitation, a wavelength versus intensity curve, or fluorescence emission spectrum, is obtained as the emission monochromator is caused to scan through its range of wavelengths. Alternately, when the output of the excitation monochromator is connected to the X input of the plotter, and the emission monochromator is set at a wavelength for maximum fluorescence, a wavelength versus intensity curve, of fluorescence excitation spectrum, is plotted as the excitation monochromator scans through its range of wavelengths.

To compensate for amplitude variations and distortion of the excitation spectrum by wavelength dependent emission of the xenon lamp and excitation monochromator, the light beam 23 is sampled by means of a beam splitter 34 and supplied to a wide-range reference photomultiplier tube 35 having a nearly flat wavelength response. The output of this photomultiplier tube is modified by function generators to form a compensating signal which is combined with the output signal from the signal photomultiplier tube 28 to obtain an output signal substantially free from excitation spectrum distortions. The use of such compensating circuitry is described in U.S. Pat. No. 3,967,113, which is assigned to the present assignees and in which the present applicant is named as co-inventor.

In accordance with the invention, an output signal indicative of the difference in spectral photofluorescent characteristics between two samples contained in individual cells or cuvettes is obtained by providing a novel cuvette positioning apparatus 40 which alternately positions first one cuvette containing a first fluid sample, and then another cuvette containing a second fluid sample, in the path of the incident light beam 23 from monochromator 22.

Figure 7:
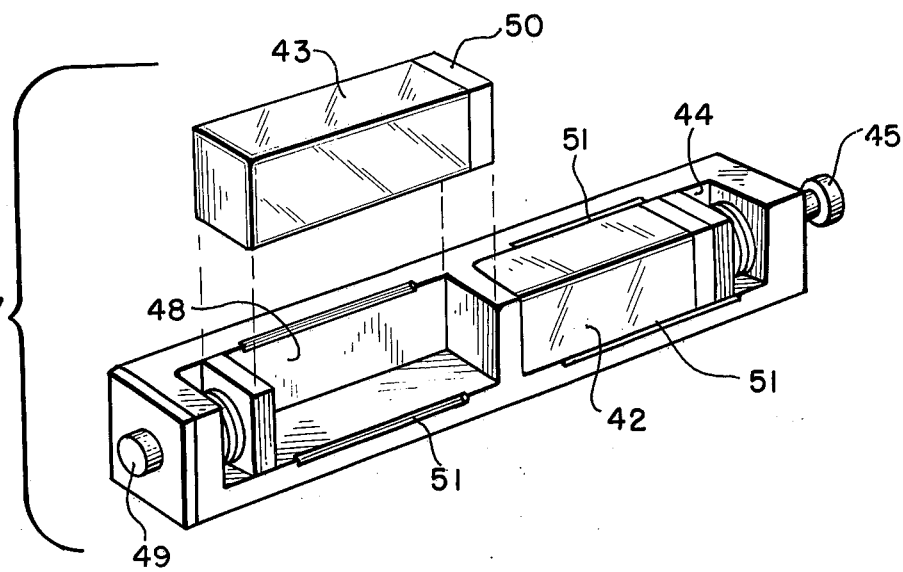
FIG. 7 is an enlarged perspective view of the cell carrier utilized in the sample positioning apparatus shown in FIGS. 3-6.

Referring to FIGS. 3–6, the cuvette positioning apparatus 40 comprises an elongated cell carrier 41 of generally square cross-section in which a first cuvette 42 containing a first sample to be analyzed, and a second cuvette 43 carrying a second sample to be analyzed, are contained. As shown in FIG. 7, the first cuvette 42 is seated in a first compartment 44 having two side walls forming flat perpendicular surfaces against which the cuvette is seated. A spring-biased plunger 45 extends through the upper end of carrier 41 and into engagement with the removable cup 46 of the cuvette to maintain the cuvette firmly seated in position. Similarly, cuvette 43 is seated in a compartment 48 located immediately beneath compartment 44 in carrier 41. Like compartment 44, compartment 48 is two perpendicular side walls for accurately positioning the cuvette. A spring-biased plunger 49 extends through the bottom end of carrier 41 and against the bottom of cuvette 43 to maintain cuvette 43 firmly seated in position with its cap 50 bearing against the top end of compartment 48. The exposed edges of compartments 44 and 48 may be provided with thumb recesses 51 to facilitate removal of the cuvettes.

Cell carrier 41 is constrained to reciprocate along a vertical path by means of a housing 52 which includes a central passageway 54 of rectangular cross-section in which the cell carrier 41 is slidably received. Reciprocative motion is imparted to cell carrier 41 by means of a drive member 60 which is reciprocatively driven in a sinusoidal manner by means including a rotatably driven drive wheel 61, a slot 62 on the drive arm, and a cam 63 on the rotating wheel. The top end of the drive member 60 is coupled to the bottom end of the cell carrier 41 by means of a magnet 64 disposed on the top end of the drive arm. The magnet, which includes a central bore for accomodating plunger 49, engages the bottom end wall of cell carrier 41 so that the carrier is forced to reciprocate with the drive arm. However, when the drive arm is not in motion, it is possible for the user to remove the cell carrier 41 by pulling upwardly with sufficient force to overcome the magnetic attraction provided by the magnet 64.

Drive arm 60 is constrained to reciprocate along a vertical axis by means of a guide block 65 and suitable supporting framework 66. Drive wheel 61 is mounted on the shaft 67 of a drive motor 68, which is mounted to framework 66 by means of a bracket 69.

The excitation light beam 23 is caused to pass through a narrow slit 70 (FIG. 5) provided in a baffle 71 mounted in the side wall of housing 52. Similarly, the emission light beam 25 is caused to pass through a slit 72 (FIG. 5) provided in a baffle 73 mounted in the housing.

To maintain the cuvette accurately seated in position in the cell carrier 41, alignment means in the form of a spring-biased plunger 74 are provided in housing 52. The plunger 74 bears against the exposed edges of the cuvettes, thus serving to maintain the cuvettes seated in cell carrier 41 and to maintain the cell carrier 41 seated in channel 53 of housing 52. Accurate alignment of the cuvette during operation of the spectrofluorometer is necessary to ensure transparency of the cuvette side walls to the excitation and emission light beams, which is possible only if a perpendicular relationship is maintained between the beams and the side walls.

In operation, drive wheel 61 is rotatably driven and drive member 60 is caused to reciprocate up and down as cam 63 moves along slot 62. This causes cuvette 42 and 43 to alternately be positioned behind baffles 71 and 73; first cuvette 43 as shown in FIG. 3, and then cuvette 42 as shown in FIG. 4. By reason of the vertical positioning of the cuvettes, and the sinusoidal reciprocation imparted by the cam and slot drive arrangement, the residence time of the respective cuvettes behind the baffles constitutes a relatively large proportion of the total cycle time, thus providing a greater useful portion of the cycle in which measurements of the samples can be made and a lower signal-to-noise ratio in the ultimate measurement.

In one successful embodiment of the invention, two standard cuvettes of approximately 1.85 inches overall length are reciprocated a total distance of approximately 1.5 inches at a speed of approximately 3.3 cycles per second. The speed and distance of travel are selected so that the samples never experience negative gravitational loading and therefore never cavitate. For a 0.75 inch spacing between the axis of drive wheel 61 and cam 63, the maximum speed of wheel 61 at which cavitation is avoided is 216 rpm. This provides a maximum acceleration to the cuvettes of 32 ft/sec$^2$ and a reciprocation rate of 3.6 cycles per second.

To provide synchronization signals for the demodulation circuitry utilized in conjunction with the spectroflourometer for demodulating the alternate time-multiplexed sample measurements into a single differential output signal, the sample positioning assembly 40 includes a pair of position transducers 80 and 81 which are actuated by an arm 82 carried on the cuvette carrier drive arm 60. These position transducers, which may be conventional optical type transducers having their own light source for detecting the proximity of arm 82, are preferably adjustable along the axis of reciprocation to allow a close correspondence to be obtained between the cuvettes being in position and the presence of a synchronizing signal.

Figure 8:
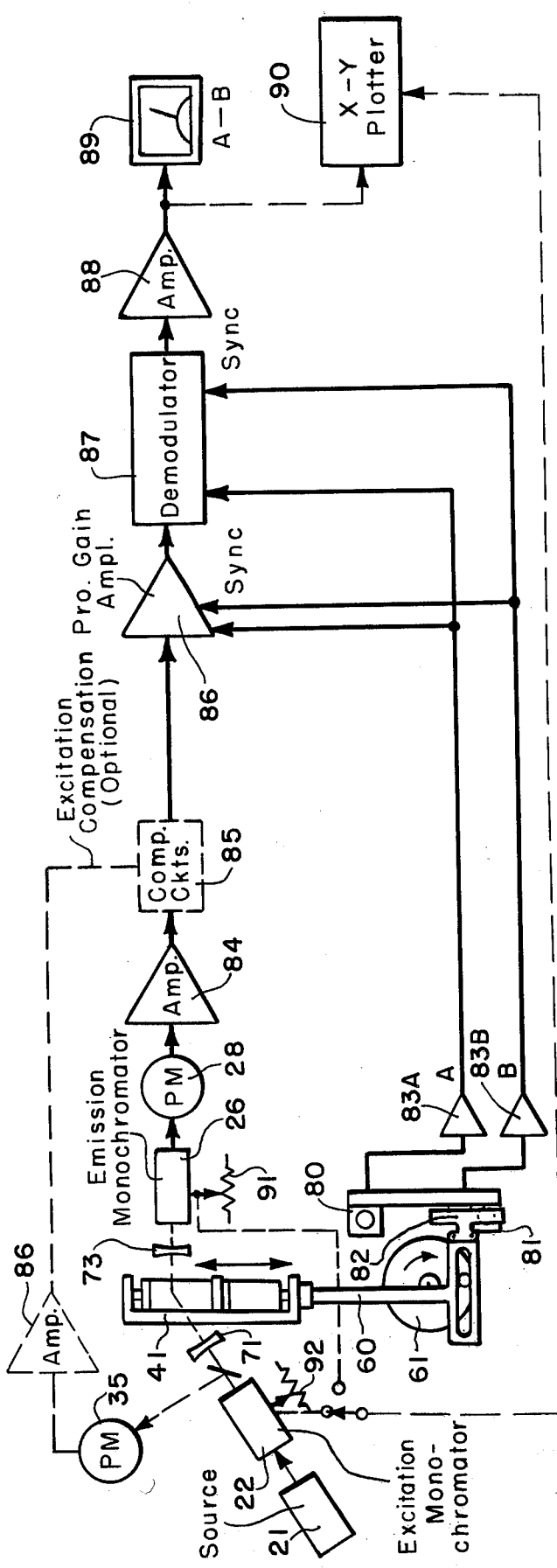
FIG. 8 is a functional block diagram of a spectrophotometric comparison system constructed in accordance with the invention.

Referring to FIG. 8, the output of position detector 80, representing positioning of the lower cuvette 43 in the light beam, is amplified by an amplifier 83A to develop an A synchronizing signal, and the output of detector 81, representing the positioning of cuvette 42 for measurement, is amplified in an amplifier 83B to develop a B synchronizing signal.

The output of photomultiplier tube 28 is applied to an amplifier stage 84, wherein the current output of the tube is converted to an analog voltage. After application to suitable noise rejection circuitry, the analog signal may be applied to a compensating circuit 85 wherein the output of the reference photomultiplier tube 35, after amplification in an amplifier 86, may be selectively combined to compensate for non-linearities and amplitude variations in the excitation source.

The compensated analog signal is applied to a programmable gain amplifier 86 which provides a variable gain factor dependent on the presence of the A and B synchronizing signals from amplifiers 83A and 83B. This allows the gain provided by this amplifier for each of the samples to be independently adjusted to achieve any scale factor changes which may be necessitated by chemical differences in the samples.

The gain-corrected signal is applied to a demodulator 87 wherein the time-multiplexed signal is converted to a continuous analog output signal indicative of the difference in the spectrofluorometric characteristics between the samples. This output signal is amplified in an amplifier 88 and applied to a suitable indicating instrument, such as the meter 89 and the X-Y plotter 90 shown. In the case of the X-Y plotter, an X axis input signal is derived from a position transducer in the form of either a potentiometer 91 coupled to the grating 33 of the emission monochromator 26, or a potentiometer 92 coupled to the grating 32 of the excitation monochromator 22, the Y axis input signal being derived from amplifier 88.

Figure 9:
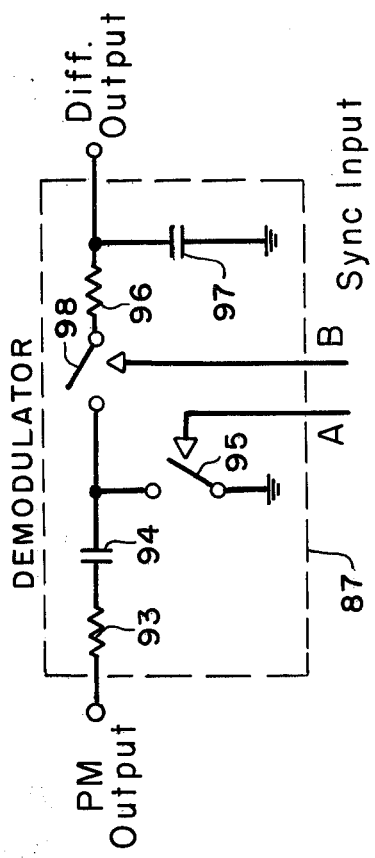
FIG. 9 is a simplified schematic diagram of a demodulator circuit for use in the spectrophotometric comparison system shown in FIG. 8.

Referring to FIG. 9, in accordance with another aspect of the invention, the modulator 87 may comprise a first voltage storage circuit comprising an impedance 93, a capacitor 94 and a switch device 95, and a second voltage storage circuit comprising an impedance 96, a capacitor 97 and a switch device 98. In operation, in the presence of an A synchronizing signal indicating that the lower cuvette is in position, switch 95 is closed by the A synchronizing signal and capacitor 94 is caused to charge to the then existing voltage level developed by photomultiplier tube 28. As lower cuvette 43 moves out of the measurement position, switch 95 opens and capacitor 94 retains the then existing charge notwithstanding subsequent variations in the voltage level of the applied analog signal.

Subsequently, when the upper cuvette 42 comes into position, the B synchronizing signal closes switch 98 to place capacitor 97 and impedance 96 into series with capacitor 94 and impedance 93. This has the effect causing a voltage level to be developed across capacitor 97 representative of the difference between the previously applied A signal generated by cuvette 42. As a result, the signal level applied to amplifier 88, and hence to the various indicating instruments connected to the system, constitutes the differential or A–B signal desired for comparison purposes.

Figure 10:
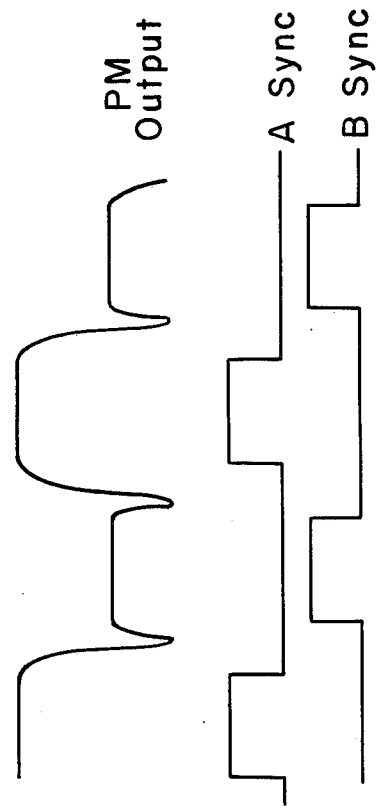
FIG. 10 depicts waveforms useful in explaining the operation of the demodulator circuit shown in FIG. 9.

The relationship between the A and B synchronizing signals generated by photomultiplier tube 28 is shown in FIG. 10. There it is seen that the signal from photomultiplier tube 28 is constant only during that portion of the measuring cycle in which one of the cuvettes is positioned in the path of the light beam. To prevent the erroneous signals generated during the transition portions of each cycle detectors 80 and 81 are positioned to provide A and B output signals only during those portions of the cycle in which the respective cuvettes are in position for measurements. To obtain the greatest possible measurement efficiency, the positioning of the detectors is such that the greatest possible portion of the photomultiplifer output signal will be recognized. To this end, detectors 80 and 81 may be positioned to allow measurement of the cuvettes while they are in motion. With standard cuvettes such as those previously described and the 1.5 inch stroke cited as an example a distance of approximately 0.45 inches may be traversed by each cuvette while providing a valid output reading, leaving only a distance of 0.3 inches in which a valid reading cannot be obtained from either cuvette. Thus, for the 1.5 inch cycle the cuvettes can move 0.9 inches while being read. This, coupled with the sinusoidal reciprocation imparted to the cell carrier, provides in each cycle an active measuring portion of approximately 74 percent and an inactive transit portion of approximately 26 percent.

The invention provides a system and apparatus for accurately and efficiently comparing spectrofluorescence in two samples. By vertically positioning the cuvettes, and sinusoidally driving the cuvette carrier, the cuvettes are caused to reside in reading positions for the longest possible period of time without introducing cavitation to the samples undergoing analysis.

While the invention has been shown in conjunction with a spectrofluorometer application, it will be appreciated that the system can be used in any spectrophotometric application wherein the light transmission, reflection, emission or absorbance characteristics of two fluid samples must be compared efficiently and accurately.

While a single embodiment of the invention has been shown and described, it will be obvious to those skilled in the art that changes and modifications may be made without departing from the invention in its broader aspects. For example, the size and shape of the cuvette carrier and its drive assembly may be changed, and the arrangement and orientation of the spectophotometric apparatus with which the cuvette positioning assembly is utilized may be changed to suit particular applications. Therefore, the aim in the appended claims is to cover all such changes and modifications which fall within the true spirit and scope of the invention.

I claim:

1. A spectrophotometer for alternately analyzing first and second material samples contained in individual cells including, means for forming an excitation radiation beam for application to a selected one of said samples, means for collecting an emission radiation beam from said selected one of said samples, means for detecting said emission radiation beam, means for positioning said samples in the path of said radiation beam including a cell carrier for supporting said cells in a substantially vertical relationship, said cells comprising elongate cuvettes of generally rectangular cross-section disposed in said cell carrier end-to-end and said cell carrier including a pair of complimentary dimensioned compartments for receiving said generally rectangular cuvettes with each compartment being configured in a manner to facilitate insertion and removal of said cuvette in and from said cell carrier and to facilitate impingement of said excitation radiation beam on, and emission of said emission radiation beam from, said samples, means for mounting said cell carrier in a substantially vertical operating path whereby one cell is disposed in the path of said excitation radiation beam at one position of travel and the other cell is disposed in the path of said excitation radiation beam at another position of travel, and drive means for reciprocating said cell carrier along said vertical operating path to alternately position said cells in said excitation radiation beam path.

2. The spectrophotometer as defined in claim 1, wherein said excitation beam impinges on each of said samples at an angle of approximately 90° to the path of said emission radiation beam.

3. The spectrophotometer as defined in claim 1 wherein said compartments are open on two sides to facilitate insertion and removal of said cuvettes in and from said cell carrier.

4. The spectrophotometer as defined in claim 1 wherein said drive means impart sinusoidal motion to said cell carrier along said defined operating path.

5. The spectrophotometer as defined in claim 4 wherein said drive means include a drive member operatively engaged to said cell carrier for reciprocation along a vertical axis therewith, and a rotatably driven wheel having a cam radially spaced thereon operatively engaged to a substantially horizontal drive slot on said drive member.

6. The spectrophotometer as defined in claim 1 wherein said drive means include a drive member mounted for reciprocation along said vertical axis, and said drive member is operatively engaged to said cell carrier by means including a magnet.

7. The spectrophotometer as defined in claim 1 wherein said cell carrier includes spring means for retaining said cells in position.

8. The spectrophotometer as defined in claim 1 wherein said drive means include means responsive to the position of said cell carrier along said operating path for generating a control effect indicative of the position thereof for application to external processing circuitry.

9. A spectrophotometer for optically analyzing first and second material samples contained in individual cells comprising, in combination: means for generating an analytical radiation beam for application to said samples; means for collecting an emission radiation beam from each of said samples; a cell carrier for supporting said cells in vertically aligned relationship, said cell carrier having two compartments, one located above the other, and each being configured in a manner to facilitate insertion and removal of said cells into and out of said compartments and to facilitate impingement of said analytical radiation beam on and collection of said emission radiation beam from each of said samples; means for mounting said cell carrier in a vertical path of reciprocation whereby said cells are individually exposed to said analytical radiation beam as said cell carrier traverses said path; and drive means for reciprocating said cell carrier along said path to alternately expose said cells to said analytical radiation beam.

10. The spectrophotometer as defined in claim 9 wherein said drive means impart sinusoidal motion to said cell carrier.

11. A spectrofluorometer for analyzing first and second material samples contained in individual cells including means for generating an excitation radiation beam for application to said samples, mean for collecting an emission radiation beam from each of said samples, a detector for analyzing said emission radiation beam received from said samples, means for alternately positioning said samples in said radiation beam including a cell carrier for supporting said cells in a substantially vertical relationship, means for mounting said cell carrier for movement in a substantially vertical operating path whereby said first cell is disposed in said excitation radiation beam at one particular position of travel, and said second cell is disposed in said excitation radiation beam at another position of travel, said cells comprising elongate cuvettes of generally rectangular cross-section disposed in said cell carrier end-to-end, one above the other and said cell carrier including a pair of complementary dimensioned compartments for receiving said generally rectangular cuvettes with each compartment being configured in a manner to facilitate insertion and removal of said cuvettes in and from said cell carrier and to facilitate impingement of said excitation radiation beam on, and emission of said emission radiation beam from said samples, drive means for reciprocating said cell carrier along said operating path to alternately position said first and second cells in said radiation path, and signal processing means for developing an output signal indicative of the variation in characteristics between said samples, said processing means including, in combination: a first storage circuit serially including a first capacitor and a first switching means coupled between said detector and a plane of reference potential; a second storage circuit serially including a second switching means and a second capacitor coupled between the juncture of said first capacitor and said first switching means, and said plane of reference potential; synchronizing means responsive to the position of said cell carrier for selectively closing said first switching means only while said first cell is in said radiation beam, and for selectively closing said second switching means only while said second cell is in said radiation beam; and utilization means including an amplifier coupled to said second capacitor and said plane of reference potential for developing a differential output signal.

12. The spectrofluorometer as defined in claim 11 wherein said first and second storage circuits each include a series impedance.

13. The spectrofluorometer as defined in claim 11, wherein said excitation beam inpinges on each of said samples at an angle of approximately 90° to the path of said emission radiation beam.

* * * * *